(12) United States Patent
Cohen et al.

(10) Patent No.: US 8,529,537 B2
(45) Date of Patent: Sep. 10, 2013

(54) ABSORBENT ARTICLE WITH ENCLOSURES

(75) Inventors: Jason C Cohen, Appleton, WI (US); Kenneth Thomas Borowski, Neenah, WI (US); Rodney Lee Miller, Jr., Shiocton, WI (US); Martin Joseph Garofalo, Menasha, WI (US); David William Koenig, Menasha, WI (US); Tatum Marie Jelenc, Chilton, WI (US); Eric Donald Johnson, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1365 days.

(21) Appl. No.: 11/198,139

(22) Filed: Aug. 5, 2005

(65) Prior Publication Data

US 2007/0032769 A1 Feb. 8, 2007

(51) Int. Cl.
*A61F 13/15* (2006.01)
(52) U.S. Cl.
USPC .......................................... 604/391
(58) Field of Classification Search
USPC ............... 604/385.06, 385.13, 391; 206/440, 206/494, 438; 66/194
See application file for complete search history.

(56) References Cited

U.S. PATENT DOCUMENTS

| | | | |
|---|---|---|---|
| 2,891,396 A * | 6/1959 | MacCaffray, Jr | 66/85 R |
| 2,971,359 A * | 2/1961 | Hubbard | 66/84 R |
| 3,442,101 A * | 5/1969 | Ploch et al. | 66/194 |
| 3,914,483 A | 10/1975 | Stipek, Jr. | |
| 3,925,585 A | 12/1975 | Aoyagi | |
| 4,100,324 A | 7/1978 | Anderson et al. | |
| 4,221,221 A | 9/1980 | Ehrlich | |
| 4,417,894 A | 11/1983 | Norris | |
| 4,702,378 A | 10/1987 | Finkel et al. | |
| 4,738,678 A | 4/1988 | Paulis | |
| 4,743,240 A | 5/1988 | Powell | |
| 4,753,647 A | 6/1988 | Curtis | |
| 4,790,840 A | 12/1988 | Cortina | |
| 4,808,175 A | 2/1989 | Hansen | |
| 4,821,439 A | 4/1989 | Wilck | |
| 4,917,693 A * | 4/1990 | Terry | 604/385.06 |
| 4,931,052 A | 6/1990 | Feldman | |
| 4,934,535 A | 6/1990 | Muckenfuhs et al. | |
| 5,037,414 A * | 8/1991 | Booth | 604/385.13 |
| D324,567 S | 3/1992 | Leslie et al. | |
| D334,426 S | 3/1993 | Meis | |
| D343,233 S | 1/1994 | Lanmon et al. | |
| 5,304,158 A | 4/1994 | Webb | |
| 5,335,372 A * | 8/1994 | Wiedner et al. | 2/457 |
| 5,350,067 A | 9/1994 | Beltran | |
| 5,447,227 A | 9/1995 | Kosberg | |
| D366,315 S | 1/1996 | Oranday | |

(Continued)

FOREIGN PATENT DOCUMENTS

DE 299 14 539 U1 2/2000
EP 0 283 064 81 4/1992

(Continued)

*Primary Examiner* — Melanie Hand
(74) *Attorney, Agent, or Firm* — David J. Arteman

(57) ABSTRACT

An absorbent article comprises a bodyside liner, an outer cover, an absorbent body located between the bodyside liner and the outer cover, and an enclosure. The enclosure comprises a cover and backing joined together to form a pocket with an object disposed therein. The enclosure is joined with the absorbent article and is adapted to transition from a closed condition to an open condition such that the object disposed within the enclosure may be accessed.

6 Claims, 7 Drawing Sheets

(56) References Cited

U.S. PATENT DOCUMENTS

| | | |
|---|---|---|
| 5,509,808 A | 4/1996 | Bell |
| 5,569,230 A | 10/1996 | Fisher et al. |
| 5,582,605 A | 12/1996 | Lepie |
| 5,702,379 A | 12/1997 | Preiss |
| 5,725,382 A | 3/1998 | Walter et al. |
| D412,982 S | 8/1999 | Wyatt |
| 5,972,041 A | 10/1999 | Smith et al. |
| 6,101,366 A * | 8/2000 | Castillo .................. 434/308 |
| D431,649 S | 10/2000 | Hunsucker |
| 6,132,474 A | 10/2000 | Smith et al. |
| 6,383,592 B1 | 5/2002 | Lowry et al. |
| 6,454,748 B1 * | 9/2002 | Ives ..................... 604/385.06 |
| 6,460,702 B2 | 10/2002 | Hammond |
| 6,544,604 B2 | 4/2003 | Matsui et al. |
| 6,572,575 B1 | 6/2003 | Shimada et al. |
| D476,741 S | 7/2003 | Childress |
| 6,594,927 B2 | 7/2003 | Witkowski |
| 6,596,918 B1 | 7/2003 | Wehrle et al. |
| 6,712,801 B1 | 3/2004 | Richardson |
| 6,785,921 B1 | 9/2004 | Conforti |
| 6,923,798 B2 * | 8/2005 | Heden et al. .................. 604/391 |
| 2002/0004656 A1 | 1/2002 | Khan et al. |
| 2002/0169431 A1 * | 11/2002 | Kline et al. ............ 604/385.03 |
| 2003/0045853 A1 * | 3/2003 | Sauer ..................... 604/385.19 |
| 2003/0065301 A1 * | 4/2003 | Elliott et al. ............. 604/385.06 |
| 2003/0073966 A1 | 4/2003 | Sosalla et al. |
| 2003/0105443 A1 | 6/2003 | Ohnishi et al. |
| 2003/0109841 A1 * | 6/2003 | Edwards ................. 604/385.06 |
| 2003/0217489 A1 | 11/2003 | Witkowski |
| 2004/0092901 A1 * | 5/2004 | Reece et al. ............. 604/385.06 |
| 2004/0127866 A1 | 7/2004 | Odorzynski et al. |
| 2004/0222119 A1 * | 11/2004 | Alexander et al. ............ 206/494 |
| 2005/0079322 A1 | 4/2005 | Knoerzer et al. |
| 2005/0149389 A1 | 7/2005 | Odorzynski |
| 2006/0020252 A1 * | 1/2006 | Strong ................... 604/385.13 |
| 2007/0032768 A1 | 2/2007 | Cohen et al. |

FOREIGN PATENT DOCUMENTS

| | | |
|---|---|---|
| GB | 2 226 297 A | 6/1990 |
| GB | 2 298 354 A | 9/1998 |
| GB | 2 299 273 A | 10/1998 |
| GB | 2 389 300 A | 12/2003 |

* cited by examiner

ABSORBENT ARTICLE WITH ENCLOSURES

BACKGROUND OF THE INVENTION

Disposable absorbent articles have typically been constructed to fasten about the waist and legs of a user to contain and absorb body exudates such as, for example, urine and feces. The disposable absorbent articles have typically included topsheets, backsheets and absorbent structures. Additionally, some disposable absorbent articles have included flaps, cuffs, fasteners, elastics, and other components, to improve the containment and absorption of body exudates and to improve the aesthetics of the articles.

Some patents and applications have suggested that absorbent articles, such as disposable diapers, may be adapted to include containers and/or pockets filled with powders, towels and baby oils and other accessories useful for baby hygiene. However, these containers and/or pockets are merely appended to the internal or external surfaces of the articles without regard to functionality or aesthetics of the absorbent article.

Therefore, there is a need to provide an absorbent article including an enclosure adapted to contain one or more objects wherein the enclosure is functionally and aesthetically integrated into the design of the absorbent article.

SUMMARY OF THE INVENTION

In response to this need, an absorbent article includes an outercover, a bodyside liner, an absorbent core positioned between the outercover and the bodyside liner, a front waist region, a rear waist region, and at least one elastic enclosure. The elastic enclosure is operatively joined to at least one waist region to define a pocket and an object is disposed within the pocket.

In various embodiments, the elastic enclosure is adapted to function as a waist elastic member or as a fastener landing material.

In various embodiments, the enclosure has a closed condition and an open condition. The elastic enclosure may provide elasticity to the absorbent article when the enclosure is in the closed condition and when the enclosure is in the open condition.

In various embodiments, the object disposed within the pocket is self contained within a package.

In various embodiments, the absorbent article may further define a longitudinal direction and a lateral direction. The enclosure may include a pull open seam and may define an open condition and a closed condition. In the closed condition, the pull open seam is intact and the object disposed within the enclosure is inaccessible. The pull open seam is manually separable thereby transitioning the enclosure from the closed condition to the open condition. In the open condition, the object disposed within the pocket is accessible.

In various embodiments, the pull open seam may be generally oriented in the lateral direction. In various embodiments, the object is a wipe. In various embodiments, the enclosure includes thermal conductive materials.

In another aspect, an absorbent article has a front portion and a rear portion. The absorbent article includes an outercover, a bodyside liner, an absorbent core positioned between the outercover and the bodyside liner, and a fastening system. The fastening system includes a pair of hook fasteners operatively joined to the absorbent article in the rear portion and a loop fastener landing material operatively joined to the outercover in the front portion to form an enclosure. The enclosure defines a pocket having at least one pull open seam, a closed condition and an open condition. The pull open seam is manually separable and adapted to transition the enclosure from the closed condition to the open condition upon separation. The pocket includes at least one wipe disposed therein. The wipe is inaccessible when the enclosure is in the closed condition and the wipe is accessible when the pocket is in the open condition.

In various embodiments, the absorbent article has a longitudinal direction and a lateral direction and the seam is generally oriented in the lateral direction.

In various embodiments, the fastener landing material is adapted to engage the fasteners after the seam has been separated.

In various embodiments, the wipe disposed within the pocket is self contained within a package.

In various embodiments, the pull open seam is a lap seam, zipper seam or line of weakness seam. In some embodiments, the pull open seam is a lap seam joined with cohesive and the enclosure is adapted to transition from the open condition to the closed condition.

In various embodiments, the enclosure may include elastic materials.

In another aspect, an absorbent article has a front portion and a rear portion. The absorbent article includes an outercover, a bodyside liner, an absorbent core positioned between the outercover and the bodyside liner and an enclosure operatively joined to the outercover in the front waist region. The enclosure includes a sub-cover having a periphery. The sub-cover is joined with a backing about the periphery to define a pocket. The sub-cover has an opening adapted to provide access to the pocket. A cover having a periphery is operatively joined to the sub-cover around the periphery. The cover spans the opening and closes the pocket. The cover is a loop landing material and at least one wipe is disposed within the pocket. A fastening system includes a pair of hook fasteners operatively joined to the absorbent article in the rear portion and adapted to engage the loop landing material.

In various embodiments, the enclosure includes thermal conductive materials.

In various embodiments, the cover is joined with the sub-cover by a cohesive and is adapted to transition the enclosure from the open condition to the closed condition.

In various embodiments, the backing, sub-cover and cover are vapor permeable.

In various embodiments, the wipe disposed within the pocket is self contained within a package.

DETAILED DESCRIPTION OF THE DRAWINGS

The present invention provides absorbent articles having covers joined to backings to create enclosures. The enclosures define pockets having objects disposed therein. The covers and/or backings may function as absorbent article components, such as, for example, a fastener landing material or a waist elastic material while containing one or more objects therein.

The absorbent article of the present invention will be described in terms of a diaper adapted to be worn by infants about the lower torso. It is understood that the absorbent article of the present invention is equally applicable to other articles such as adult incontinent products, training pants, feminine care products, and the like.

As used herein, the term "join", and derivatives thereof, encompasses configurations wherein an element is directly secured to another element by affixing the element directly to the other element and configurations wherein the element is indirectly secured to the other element by affixing the element to intermediate member(s) which in turn are affixed to the other element.

Figure 1:
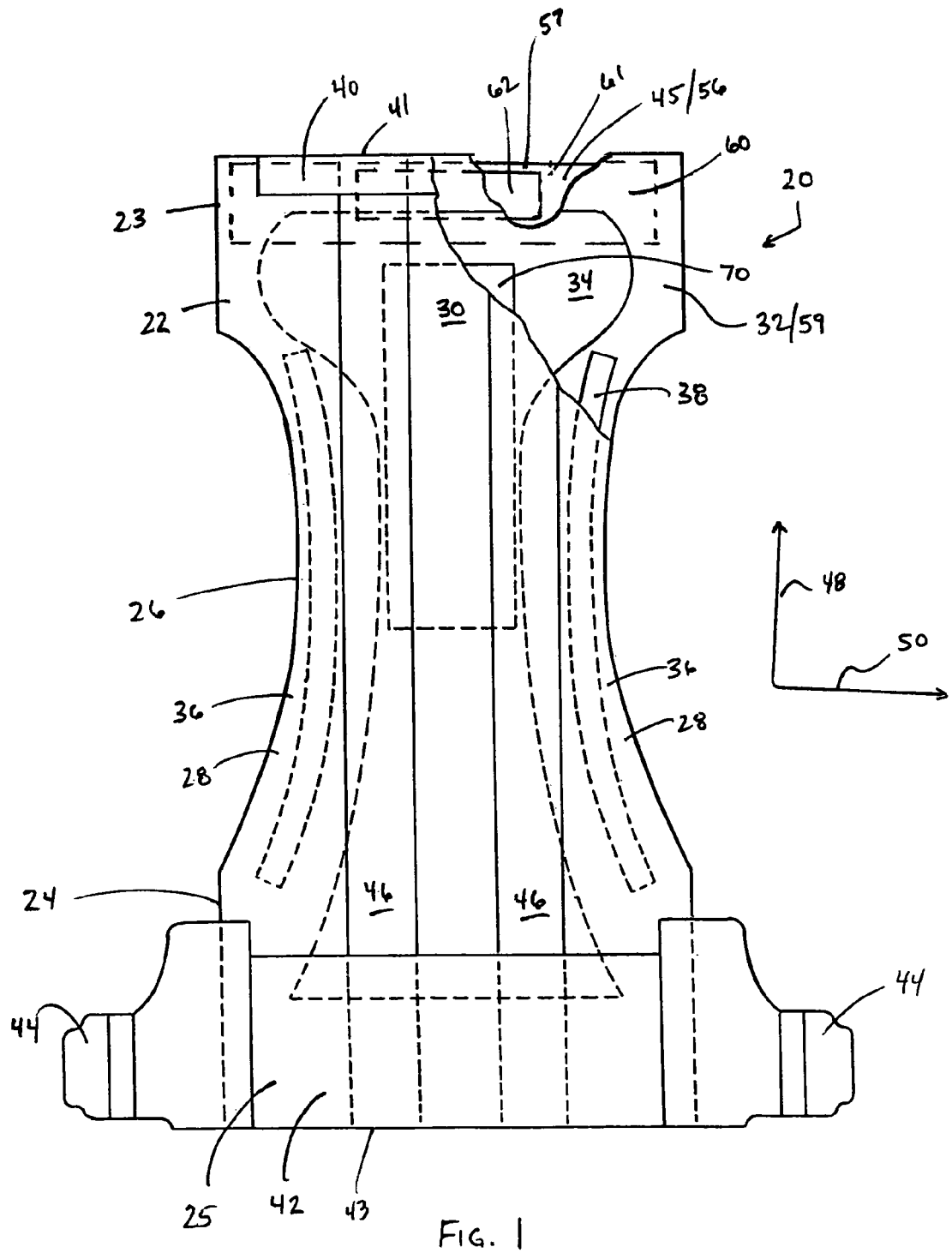
FIG. 1 representatively illustrates a partially cut away, top plan view of an exemplary absorbent article in a stretched and laid flat condition with the surface of the article that contacts the skin of the wearer facing the viewer.

FIG. 1 representatively illustrates an embodiment of an absorbent article 20 of the present invention. The surface of the article which contacts the wearer is facing the viewer. The absorbent article 20 defines a front portion 22, a rear portion 24 and a crotch portion 26 connecting the front portion 22 and the rear portion 24. The front portion 22 defines a front waist region 23 and includes a front waist edge 41. The rear portion 24 defines a rear waist region 25 and includes a rear waist edge 43. The absorbent article 20 also defines a longitudinal direction 48 and a lateral direction 50. The absorbent article 20 includes a bodyside liner 30, an outer cover 32 and an absorbent core 34 located between the bodyside liner 30 and the outer cover 32.

The absorbent article 20 also includes one or more enclosures 60. The enclosures 60 include at least one cover 56 joined about a cover periphery 57 to at least one backing 59. The enclosures 60 define one or more pockets 61 wherein each pocket 61 has one or more objects 62 disposed therein.

As used herein, reference to a front portion refers to that part of the absorbent article which is generally located on the front of a wearer when in use. Reference to a front waist region refers to that part of the front portion which is located generally near the waist opening. Reference to the rear portion refers to the portion of the article generally located at the rear of the wearer when in use. Reference to a rear waist region refers to that part of the rear portion which is located generally near the waist opening. Reference to the crotch portion refers to that portion which is generally located between the legs of the wearer when in use.

The crotch portion 26 has opposite longitudinal side portions 28 which include a pair of elasticized, longitudinally-extending leg cuffs 36. The leg cuffs 36 are generally adapted to fit about the legs of a wearer in use and serve as a mechanical barrier to the lateral flow of body exudates. The leg cuffs 36 are elasticized by a pair of leg elastics 38. The absorbent article 20 may further include a front waist elastic 40 and/or a rear waist elastic 42. The rear portion 24 of the absorbent article 20 may further include a fastening means 44 which is adapted to hold the absorbent article 20 about the waist of the wearer when in use. The absorbent article 20 may also include a pair of containment flaps 46 which extend longitudinally along the absorbent article 20 and are also adapted to provide a barrier to the flow of body exudates. It should be recognized that individual components of the absorbent article 20, such as the elastic members, may be optional depending upon the intended use of the absorbent article 20.

As used herein, the term "elastic" and derivatives thereof refers to materials or components that are generally capable of recovering their shape after deformation when the deforming force is removed. Specifically, as used herein, the term elastic or elastomeric is meant to be that property of any material or component which, upon application of a biasing force, permits that material or component to be stretchable to a stretched, biased length, which is at least about 125 percent, that is 1.25 times, its relaxed, unbiased length, and that will cause the material to recover at least 40 percent of its elongation upon release of the stretching, elongating force.

The bodyside liner 30 of the absorbent article 20 suitably presents a bodyfacing surface which is intended to be worn adjacent the body of the wearer and is compliant, soft feeling and nonirritating to the wearer's skin. Further, the bodyside liner 30 may be less hydrophilic than the absorbent core 34, to present a relatively dry surface to the wearer, and may be sufficiently porous to be liquid permeable, permitting liquid to readily penetrate through its thickness. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearer's skin from fluids held in the absorbent core 34.

Various woven and nonwoven fabrics can be used for the bodyside liner 30. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity.

The outer cover 32 of the absorbent article 20 may suitably be composed of a material which is either liquid permeable or liquid impermeable. It is generally preferred that the outer cover 32 be formed from a material which is substantially impermeable to fluids. For example, a typical outer cover can be manufactured from a thin plastic film or other flexible liquid-impermeable material. For example, the outer cover 32 may be formed from a polyethylene film. If it is desired to present the outer cover 32 with a more clothlike feeling, the outer cover 32 may comprise a polyethylene film having a nonwoven web laminated to the outer surface thereof, such as a spunbond web of polyolefin fibers. Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the absorbent core 34. Still further, the outer cover 32 may optionally be composed of a micro-porous "breathable" material which permits vapors to escape from the composite absorbent core 34 while still preventing liquid exudates from passing through the outer cover 32.

The bodyside liner 30 and outer cover 32 are generally adhered to one another so as to form a pocket in which the composite absorbent core 34 is located. The bodyside liner 30 and outer cover 32 may be adhered directly to each other around the outer periphery of the absorbent article 20 by any means known to those skilled in the art such as, for example, adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 30 to the outer cover 32. Such bonding means may also be suitable for attaching other components of the composite absorbent core and absorbent article of the present invention together. The leg cuffs 36 are suitably formed by portions of the outer cover 32, and/or bodyside liner 30, which extend beyond the longitudinal sides of the composite absorbent core 34. Naturally, the leg cuffs 36 may also be formed from separate materials which are attached to the outer cover 32 and/or bodyside liner 30.

The leg cuffs 36 may include leg elastics 38. Waist elastics 40 and 42 may also be provided. The leg elastics 38 are arranged to draw and hold the absorbent article 20 against the legs of the wearer. The waist elastics 40 and 42 are also arranged to draw and hold the absorbent article 20 against the wearer. Materials suitable for use in forming leg elastics 38 and waist elastics 40 and 42 are known to those skilled in the art. Exemplary of such materials are strands or ribbons of a polymeric, elastomeric material which are adhered to the absorbent article 20 in a stretched position, or which are attached to the absorbent article while the article is pleated, such that elastic constrictive forces are imparted to the absorbent article 20. In a particular aspect of the invention, the elastics may be composed of individual strands of LYCRA which are available from INVISTA Co., a business having offices in Wichita, Kans., USA.

The leg elastics 38 and waist elastics 40 and 42 may have any configuration which provides the desired performance. For example, the leg elastics 38 and waist elastics 40 and 42 may comprise a single strand of elastic material, or may comprise several parallel or non-parallel strands of elastic material. The leg elastics 38 may be generally straight or optionally curved to more closely fit the contours of the legs and buttocks of the wearer and better contain bodily exudates. The leg elastics 38 and waist elastics 40 and 42 may be attached to the absorbent article 20 in any of several ways which are well known to those skilled in the art. For example, the elastics may be ultrasonically bonded, thermally bonded or adhesively bonded to the absorbent article 20.

The fastening means 44 are typically applied to the corners of the rear portion 24 of the absorbent article 20 to provide a means for holding the article 20 on the wearer. Suitable fastening means 44 are well known to those skilled in the art and can include tape tab fasteners, hook and loop fasteners, mushroom and loop fasteners, snaps, pins, belts, and the like, and combinations thereof. Typically, the fastening means 44 are configured to be refastenable. It should also be understood that it may be possible to dispense with the fastening means 44 in an absorbent article having a given design configuration.

In some embodiments, the fastening means 44 may be adapted to engage or otherwise join with a fastener landing material 45. Typically, the fastener landing material 45 is a loop material joined to the outercover 32 in the front waist region 23 and is adapted to engage hook-type fastening means 44. In alternative embodiments, the fastener landing material 45 may be a film adapted to engage with tape tab fastening means 44.

The absorbent core 34 is positioned between the bodyside liner 30 and the outer cover 32 to form the absorbent article 20. The absorbent core 34 is generally conformable and capable of absorbing and retaining body exudates. It should be understood that, for the purpose of the present invention, the absorbent core 34 may comprise a single, integral piece of material or, alternatively, may comprise a plurality of individual separate pieces of material which are operably assembled together.

The absorbent core 34 may have any of a number of shapes and sizes. The absorbent core 34 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 34 may also comprise selected blends of the various types of fibers mentioned above. The absorbent core 34 may include a matrix of hydrophilic fibers, such as a web of cellulosic fibers, mixed with particles of a high-absorbency material such as that commonly known as superabsorbent material.

The absorbent article 20 of the present invention may also contain a surge portion 70 to advantageously improve the overall fluid intake rate of the absorbent core 34. The surge portion 70 is typically less hydrophilic than the absorbent core 34 and is configured to collect and temporarily hold fluid surges. This configuration can also help prevent fluid exudates from pooling and collecting on portions of the absorbent core 34.

Various woven and nonwoven materials can be used to construct the surge portion 70. For example, the surge portion 70 may be a layer of a spunbonded or meltblown web of polyolefin fibers or a bonded carded web of natural and synthetic fibers. The surge portion 70 may be a substantially hydrophobic material and, optionally, can be treated with a surfactant or otherwise to impart a desired level of wettability and hydrophilicity. The surge portion 70 may also include other wettable fiber materials such as cotton, rayon, wood pulp, inherently wettable synthetic polymers, hydrophilized or surface treated polymers, and the like. The surge portion 70 may be of any desired shape and configuration.

In various embodiments, the one or more enclosures 60 may be located generally at any location on the internal or external surface of the absorbent article, such as, for example, the outercover 32, the bodyside liner 30 or both. The enclosures 60 are comprised of at least one cover material 56 and at least one backing material 59. The cover materials 56 have a cover periphery 57. As used herein, the term "periphery" describes the outward bounds of a material or object as distinguished from its internal regions. The cover materials 56 are joined with the backing materials 59 about the cover periphery 57 to form the enclosure 60. The enclosure 60 defines a pocket 61 which includes one or more objects 62 disposed therein. The objects 62 are located between one or more of the cover materials 56 and one or more of the backing materials 59.

In various embodiments, the enclosures 60 may be joined to the bodyside liner 30 and/or the outercover 32 and/or the inner surface and/or the outer surface of the absorbent article 20 by any suitable means. Desirably, the backing material 59 may be joined to the absorbent article 20 thereby leaving the cover material 56 accessible to the caregiver or user.

In various embodiments, one or more components of the enclosures 60 may be multifunctional. As used herein, the term "multifunctional" describes one or more components of an enclosure 60 that are functional in the article for reasons other than forming portions of the enclosures 60.

For example, an enclosure 60 comprising the fastener landing material 45 functioning as the cover material 56 would be considered multifunctional. Likewise, the outercover 32 functioning as the backing material 59 would be considered multifunctional. As another example, the waist elastics 40 and/or 42 may serve as the cover material 56 and the bodyside liner 30 may serve as the backing 59. In these embodiments, the waist elastics 40 and/or 42 are generally joined about the periphery 57 to the bodyside liner 30 in the front waist region 23 and/or rear waist region 25 so as to form the enclosure 60. The enclosure 60 defines a pocket 61 which contains one or more objects 62 disposed therein. The waist elastics 40 and/or 42 may be joined to the bodyside liner 30 around the outer periphery 57 of the waist elastics 40 and/or 42 by any means known to those skilled in the art such as adhesive bonds, cohesive bonds, sonic bonds, thermal bonds, mechanical bonds, and the like, and combinations thereof. For example, a uniform continuous layer of adhesive, a patterned layer of adhesive, a sprayed or meltblown pattern of adhesive or an array of lines, swirls or spots of adhesive may be used to affix the waist elastics 40 and/or 42 to the bodyside liner 30.

As another example, FIG. 1 representatively illustrates an enclosure 60 being formed by a fastener landing material 45 (functioning as the cover material 56) and an outercover 32 (functioning as the backing material 59). In this embodiment, the fastener landing material 45 is joined about the periphery 57 to the outercover 32 in the front waist region 23 to form the enclosure 60. The enclosure 60 defines a pocket 61 which contains one or more objects 62 therein.

The fastener landing material 45 may be joined to the outercover 32 by any means known to those skilled in the art such as adhesive bonds, sonic bonds, thermal bonds, mechanical bonds, and the like, and combinations thereof. For example, a uniform continuous layer of adhesive, a patterned layer of adhesive, a sprayed or meltblown pattern of adhesive or an array of lines, swirls or spots of adhesive may be used to affix the fastener landing material 45 to the outer cover 32.

In various embodiments, the enclosures 60 may contain additional layers as necessary to achieve the desired functional and/or aesthetic objectives of the designer. For example, additional layers may be added to create a cloth-like feel and/or to add elasticity and/or to alter vapor permeability and/or to alter liquid impermeability, and the like.

The materials used to make the covers 56 and/or backings 59 may be any suitable material described herein. For example, the covers 56 and/or backings 59 may be manufactured from a wide selection of web materials, such as porous foams, reticulated foams, plastic films, natural fibers, synthetic fibers, or a combination of natural and synthetic fibers. Various woven and nonwoven fabrics may be used for the covers 56 and/or the backings 59. For example, the covers 56 and/or the backings 59 may be composed of a meltblown or spunbonded web of polyolefin fibers and/or bonded carded web of natural and/or synthetic fibers. The covers 56 and/or the backings 59 may suitably be composed of a material which is either liquid permeable or liquid impermeable. The covers 56 and/or the backings 59 may suitably be composed of a material which is either vapor permeable or liquid permeable. The covers 56 and/or the backings 59 may be formed from a polyethylene film having a nonwoven web laminated to the outer surface thereof, such as a spunbonded web of polyolefin fibers. The covers 56 and/or the backings 59 may be nonextensible, extensible or elastic.

In various embodiments, the materials used to make the covers 56 and/or backings 59 may have higher thermal conductivity to facilitate the transfer of body heat to the object 62 located within the pocket 61. For example, the material used to make the covers 56 and/or backings 59 may be made from foils, nonwovens treated with thermally conductive adhesive, thermal conductive polymers, and the like, and combinations thereof. One suitable polymer is the E-SERIES Thermally Conductive Plastics available from Cool Polymers Inc., having office in Warwick, R.I., USA. In various embodiments, the adhesive or adhesives used to join the covers 56 and/or backings 59 with the article 20 may be thermally conductive, such as, for example, Thermally Conductive Tapes 9882, 9885, or 9892FR manufactured by 3M Corporation having offices in St. Paul, Minn., USA.

Figure 2:
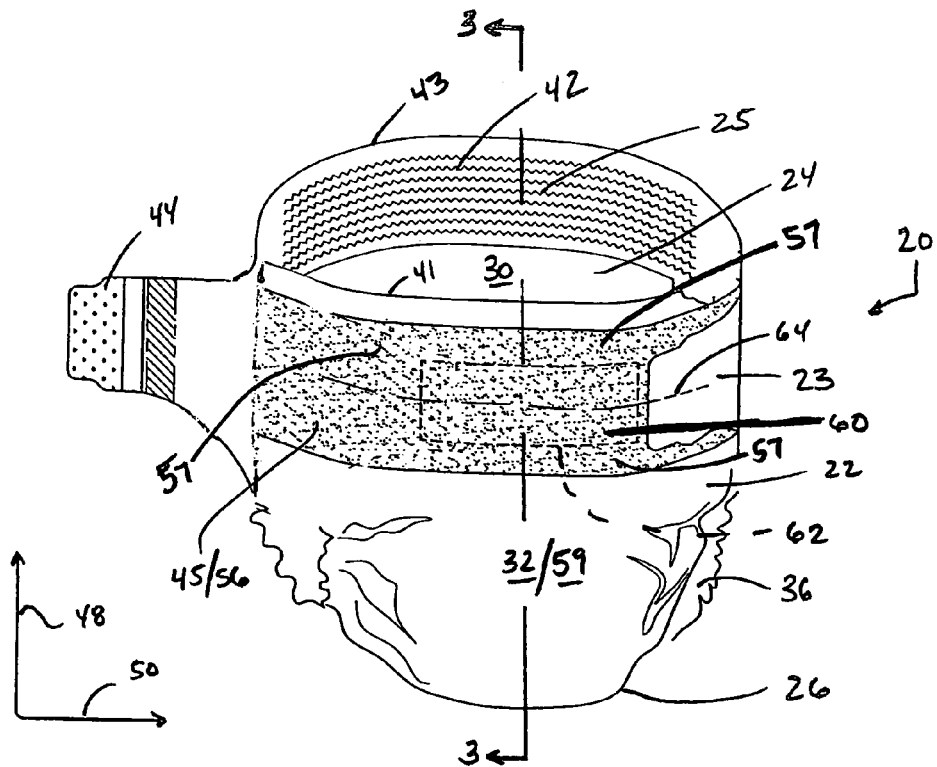
FIG. 2 representatively illustrates a front perspective view of an exemplary absorbent article having an enclosure in the closed condition.

Referring now to FIG. 2, the enclosures 60 may have one or more seams 64. The seams 64 may include pull open seams such as, for example, zipper seams, lap seams, lines of weakness seams, and the like, and combinations thereof. The seams 64 may include any closure means that allows a user to manually transition the enclosures 60 from a closed condition to an open condition. Once in the open condition, the one or more objects 62 contained within the enclosures 60 are accessible to the user. The one or more seams 64 are desirably located in the cover material 56 but may alternatively or additionally be located in the backing material 59.

As used herein, the term "pull open seam" refers to seams that can be transitioned from a closed condition to an open condition by manually applying force to the seam. Often this force involves pulling the material(s) on opposite sides of a seam in opposing directions to effect a separation.

As used herein, the term "zipper seam" refers to self-mating rib and flange seams such as are commonly used with sandwich bags. A suitable zipper seam is described in U.S. Pat. No. 6,544,604 issued Apr. 15, 2003 to Galkiewicz et al.

As used herein, the term "lap seam" refers to the joining of two or more materials in face to face relation, i.e., wherein one material "overlaps" another material. For example, the sealed flap on an envelope would be a lap seam. Depending on the type of adhesive used, the lap seam of an envelope may or may not be considered a pull open seam.

As used herein, the term "line of weakness" seam refers to a seam created in one or more pieces of material by partial pressure cutting, partial ultrasonic cutting, partial thermal deformation, mechanical thinning, perforating or other processes as are known in the art. The line of weakness seam may extend, at least partially, through the given material(s).

As used herein, the term "perforating" means to make one or more holes, slits, apertures, voids, or the like, or combinations thereof through one or more materials to facilitate separation of the one or more materials.

As used herein the term "closed condition" describes the enclosures 60 when the one or more objects located therein are not accessible to a user without destroying the enclosure 60 and/or destroying the absorbent article 20 to which the enclosure 60 is joined and/or separating one or more seams 64.

As used herein the term "open condition" describes the enclosure 60 after the one or more seams 64 are separated and when the one or more objects 62 located therein are accessible to a user.

In various embodiments, the seams 64 may be oriented generally in the longitudinal direction 48, the lateral direction 50 and combinations thereof. The seams 64 may be formed in various shapes such as, for example, T-shaped, U-shaped, V-shaped, X-shaped, Y-shaped, and the like, and combinations thereof.

In various embodiments, the seams 64 may be adapted to be resealable such that a user may transition the enclosure 60 from the closed condition to the open condition by separating the seam 64 and then transition the enclosure 60 from the open condition to the closed condition by re-joining the seam 64. In other embodiments, the seams 64 may be adapted such that once the seam is separated, the seam may not be re-joined and the enclosure 60 cannot be resealed.

In various embodiments, the seams 64 may be adapted such that once the seam 64 is separated, the enclosure 60 remains multifunctional as an absorbent article component. For example, the enclosure 60 may also be functional as a waist elastic having elasticity in the lateral direction 50. The enclosure 60 may include a seam 64 generally aligned in the lateral direction 50. When the user separates the seam 64, the waist elastic maintains its functional elasticity. In yet other embodiments, the seams 64 may be adapted such that once the seam is separated, the enclosure 60 is no longer multifunctional.

In various embodiments, the one or more seams 64 may be made more visible or prominent through the use of one or more seam indicators. The seam indicators may include printing, embossing, bonding, or the like, or combinations thereof of one or more indicia proximate the seams 64. The seam indicators are adapted to draw the caregiver's or user's attention to the seams 64 and may include shapes, symbols, text, graphics, or the like, or combinations thereof.

In various embodiments, the one or more seams 64 may include a tamper evident device, such as, for example, a color change element or a text alignment element as are known in the art.

In various embodiments, the enclosures 60 may be adapted to be removable from the absorbent article 20 without destroying the enclosure 60 or the absorbent article 20. In yet other embodiments, the enclosure 60 may be adapted to be removable from the absorbent article 20 and/or may be adapted to be rejoined to the absorbent article 20. In some embodiments, the enclosure 60 may be adapted to be removable from the absorbent article 20 and/or may be adapted to be refilled with one or more objects and/or may be adapted to be rejoined to the absorbent article 20.

In various embodiments, the objects 62 located in the enclosure 60 may include, for example, one or more wipes, lotions, creams, powders, disposal bags, oils, coupons, toys, games, stickers, sunscreens, UV detectors, perfumes, booklets, instructions, trading cards, hand sanitizers, promotional items, trial products, and the like, and combinations thereof. Additional objects suitable for placement within the enclosures are described in U.S. application Ser. No. 11/198,244 to Cohen et al. filed Aug. 5, 2005, entitled "Article with Premium", the entirety of which is incorporated herein by reference where not contradictory.

In various embodiments, the objects 62 may be wipes that are generally rectangular in shape. The wipes can have any suitable unfolded width and length. For example, the wipes can have an unfolded length of from about 2.0 to about 80.0 centimeters and desirably from about 10.0 to about 26.0 centimeters and an unfolded width of from about 2.0 to about 80.0 centimeters and desirably from about 10.0 to about 45.0 centimeters.

Materials suitable for the wipes of the present invention are well known to those skilled in the art. The wipes can be made from any material suitable for use as a wipe, including meltblown, coform, airlaid, spunlace, bonded-carded web materials, hydroentangled materials, high wet strength tissue, and the like. The material suitable for use as a wipe can comprise synthetic or natural fibers or combinations thereof. The wipes can have a basis weight of from about 25 to about 140 grams per square meter and desirably from about 40 to about 90 grams per square meter.

In a particular aspect, the wipes can comprise a coform basesheet of polymeric microfibers and cellulosic fibers having a basis weight of from about 60 to about 100 grams per square meter and desirably about 80 to 85 grams per square meter. Such coform basesheets are manufactured generally as described in U.S. Pat. No. 4,100,324 to Anderson et al. which issued Jul. 11, 1978, the entirety of which is incorporated herein by reference where not contradictory. Typically, such coform basesheets comprise a gas-formed matrix of thermoplastic polymeric meltblown microfibers, such as, for example, polypropylene microfibers, and cellulosic fibers, such as, for example, wood pulp fibers. The relative percentages of the polymeric microfibers and cellulosic fibers in the coform basesheet can vary over a wide range depending on the desired characteristics of the wet wipes. For example, the coform basesheet can comprise from about 20 to about 100 weight percent, desirably from about 20 to about 60 weight percent, and more desirably from about 30 to about 40 weight percent of polymeric microfibers based on the dry weight of the coform basesheet being used to provide the wipes.

The wipes of the different aspects of the present invention can contain a liquid which can be any solution which can be absorbed into the wipes, thus making them "wet wipes." The liquid contained within the wet wipes can include any suitable components which provide the desired wiping properties. For example, the components can include water, emollients, surfactants, preservatives, chelating agents, pH buffers, fragrances or combinations thereof. The liquid can also contain lotions, ointments and/or medicaments.

Figure 11:
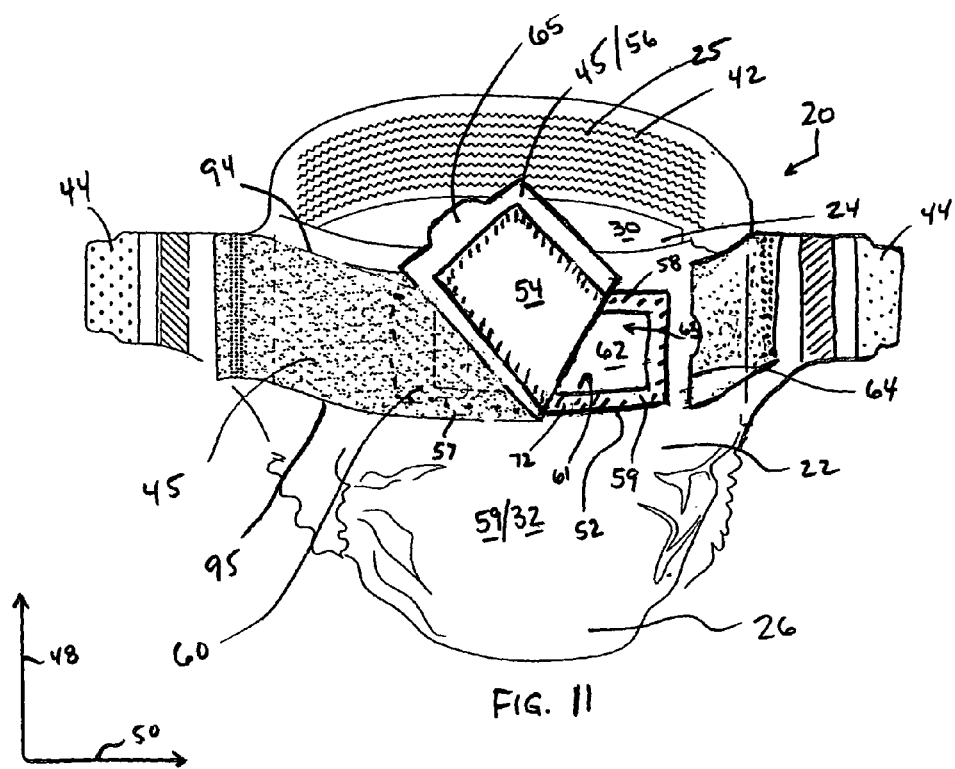
FIG. 11 representatively illustrates a front perspective view of the absorbent article of FIG. 10 with the enclosure in the open condition.

In various embodiments, the objects 62 may be self contained within a package 52 (see e.g., FIG. 11). As used herein, the term "self contained" refers to objects that are encased in a package 52 in addition to the cover material 56 and the backing material 59. For example, in some embodiments, a wet wipe may be self contained within a moisture impermeable package. The wet wipe and the packaging may then be included in the pocket 61 within the enclosure 60.

The package 52 may include one or more sub-covers 54 (see e.g., FIG. 11) and/or one or more sub-backings 58 (see e.g., FIG. 11). The sub-covers 54 may be joined about the periphery to the sub-backings 58 to define a second pocket 63 (see e.g., FIG. 11). The object 62 may then be contained within the second pocket 63 within the package 52. The package 52 may then be contained within the pocket 61 within the enclosure 60.

In various embodiments, a self contained object may be desirable for reasons of sterility, moisture retention, safety, light avoidance, air avoidance, thermal stability, and the like. In various embodiments, a self contained object may desirably maintain the efficacy of the object, such as, for example, perfumes, sunscreens, UV detectors, photo activated compounds, and the like.

Use of self contained objects 62 may also allow the cover materials 56 and/or the backing materials 59 to be selected for better performance within the absorbent article 20. For example, a wet wipe may be contained within a liquid impermeable self contained package 52. The wet wipe and self contained package may then be placed in an enclosure 60 having a liquid permeable and/or vapor permeable cover material 56 and/or backing material 59 thereby allowing the absorbent article 20 to maintain breathability in the area where the enclosure 60 is joined to the absorbent article 20 while keeping the wipe wet. Similarly, a self contained package may be desirable to block out light thereby obviating the need for the enclosure material to block light.

Figure 3:
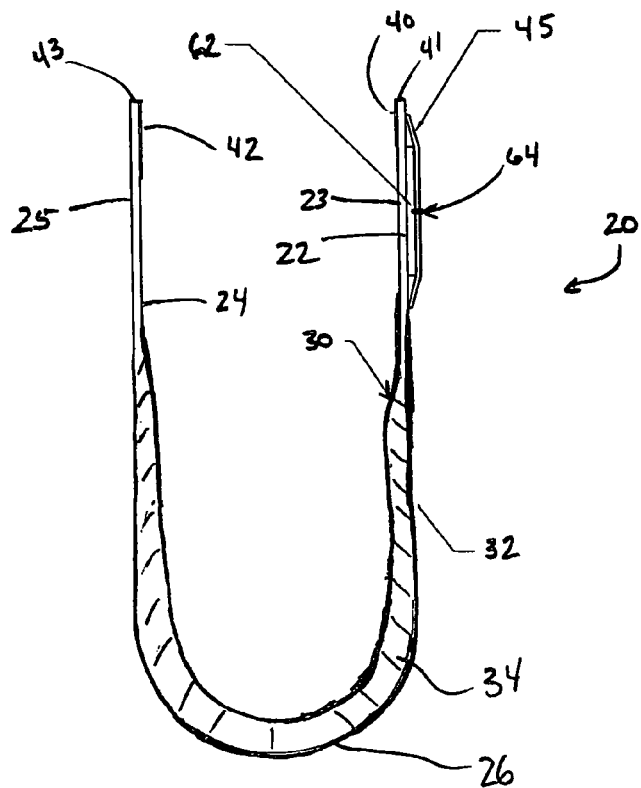
FIG. 3 representatively illustrates a cross-sectional view of the absorbent article of FIG. 2 taken along the line 3-3.

Referring now to FIG. 2, a front perspective view of an exemplary absorbent article 20 is shown in a partially fastened condition. FIG. 3 representatively illustrates a cross-sectional view of the absorbent article 20 of FIG. 2 taken along the line 3-3. The absorbent article 20 of FIGS. 2 and 3 includes a front portion 22, a rear portion 24 and a crotch portion 26. The crotch portion 26 connects the front portion 22 to the rear portion 24. The front portion 22 includes a front waist region 23. The rear portion 24 includes a rear waist region 25. The front waist region 23 includes a front waist elastic 40. The rear waist region 25 includes a rear waist elastic 42.

The absorbent article 20, in this embodiment, further includes a bodyside liner 30, an outercover 32 and an absorbent core 34 located between the bodyside liner 30 and the outercover 32. The absorbent article 20 further includes fastening means 44 located in the rear portion 24 that are adapted to join with a fastener landing material 45 located in the front portion 22. The fastener landing material 45 has a periphery 57 and is operatively joined about the periphery 57 to the outercover 32 in the front portion 22 to form an enclosure 60 which defines a pocket 61. The pocket 61 contains one or more objects 62 therein. The enclosure 60 is illustrated in a closed condition.

The enclosure 60, in this embodiment, has a single seam 64 located in the fastener landing material 45 and extending generally in the lateral direction 50. The seam 64 is line of Weakness seam.

The enclosure 60 includes an object 62, such as, for example, one or more baby wipes. A caregiver or user desiring to access the one or more objects 62 located in the enclosure 60 may manually separate the seam 64 thereby transitioning the enclosure 60 from the closed condition to the open condition. In the open condition, the one or more objects 62 may be accessed and/or removed from the enclosure 60.

In various embodiments, the object 62 may be free to move within the enclosure 60. This may be advantageous in that elastic and/or extensible materials may be used to create the cover material 56 (in this embodiment the fastener landing material 45) and/or the backing material 59 (in this embodiment the outercover 32) thereby creating an elastic and/or extensible enclosure 60. As the absorbent article 20 is used, the outercover 32 and/or the bodyside liner 30 and/or the front waist elastic 40 may extend and/or contract without inhibition from the object 62 contained within the enclosure 60 or without inhibition from the materials used to create the enclosure 60.

In various embodiments, the enclosures 60 may be elastic and/or extensible when the enclosure 60 is in the open condition and/or closed condition. The one or more seams 64 may be adapted to allow the enclosure 60 to be elastic and/or extensible both in the closed condition and in the open condition. For example, the seam 64 may extend generally in the lateral direction 50, as illustrated in FIG. 2, and the enclosures 60 may be elastic and/or extensible in the lateral direction 50. As such, even after the seam 64 is separated and the enclosure 60 is transitioned from the closed condition to the open condition, the enclosures 60 remains elastic and/or extensible.

In various embodiments, and as illustrated in FIG. 2, the enclosure 60 and/or the object 62 may be centered in the lateral direction 50.

Figure 4:
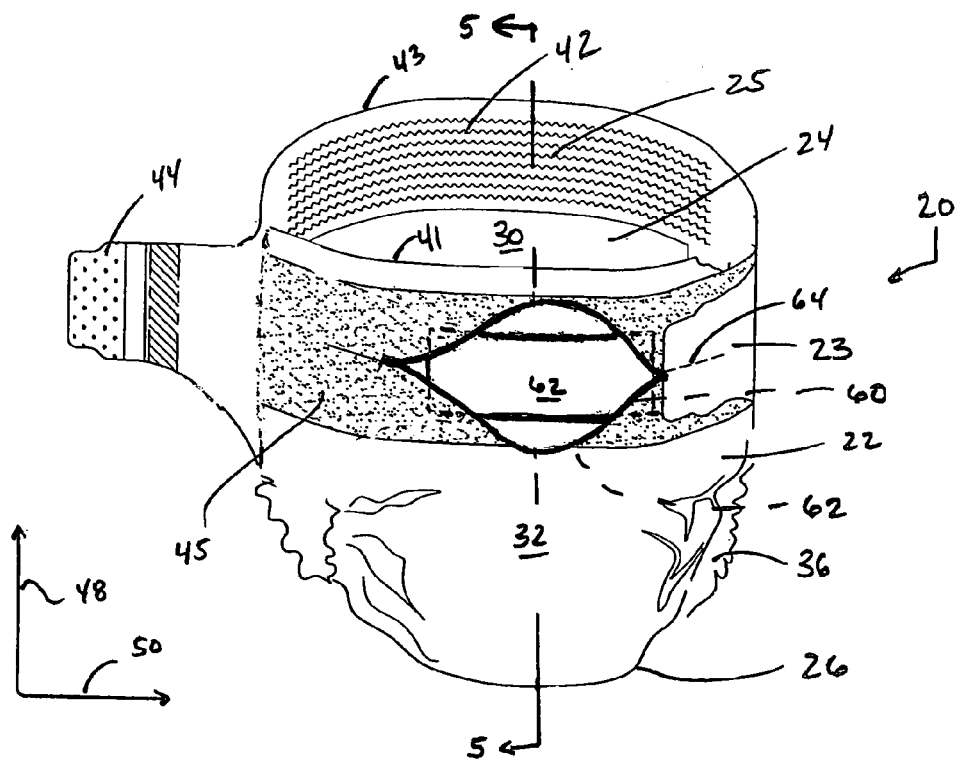
FIG. 4 representatively illustrates a front perspective view of the absorbent article of FIG. 2 with the enclosure in the open condition.
Figure 5:
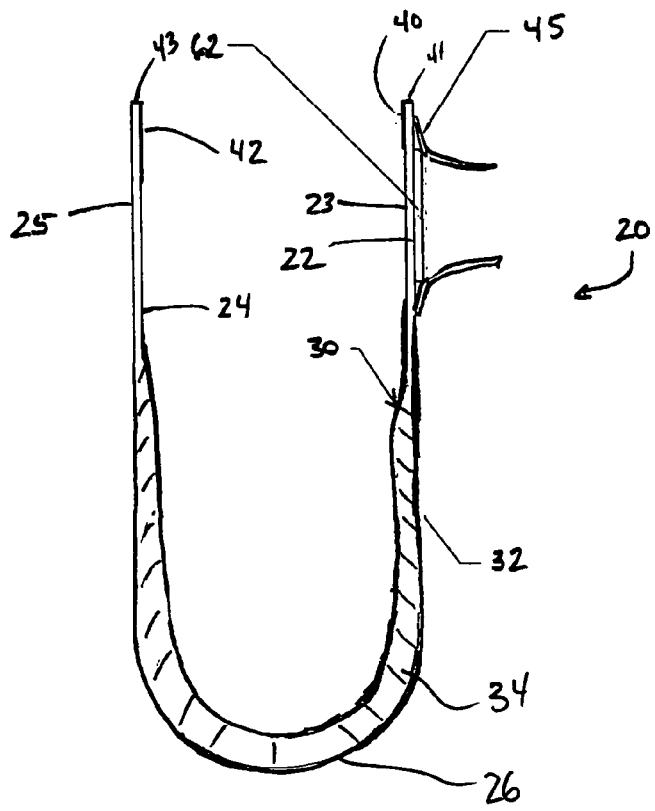
FIG. 5 representatively illustrates a cross-sectional view of the absorbent article of FIG. 4 taken along the line 5-5.

Referring now to FIG. 4, a front perspective view of the absorbent article 20 of FIG. 2 is shown in a partially fastened condition with the enclosure 60 in the open condition thereby allowing access to the object 62 contained therein. FIG. 5 representatively illustrates a cross-sectional view of the absorbent article 20 of FIG. 4 taken along the line 5-5.

Figure 6:
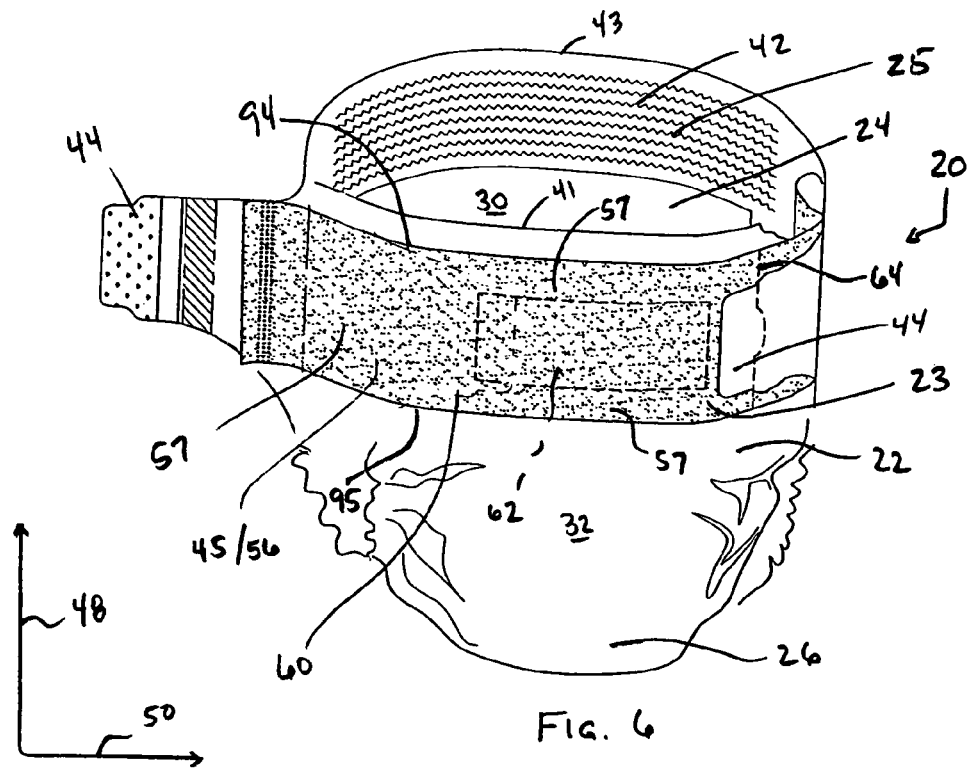
FIG. 6 representatively illustrates a front perspective view of an exemplary absorbent article having an enclosure in the closed condition.

Referring now to FIG. 6, a front perspective view of an exemplary absorbent article 20 is shown in a partially fastened condition. Similar to the absorbent article 20 of FIG. 2, the absorbent article 20 of FIG. 6 includes a front portion 22, a rear portion 24, a crotch portion 26, a front waist region 23, a rear waist region 25, and a rear waist elastic 42. The absorbent article 20 further includes a bodyside liner 30, an outercover 32 and an absorbent core 34 located between the bodyside liner 30 and the outercover 32. The absorbent article 20 further includes fastening means 44 located in the rear portion 24 that are adapted to join with a fastener landing material 45 located in the front portion 22.

The fastener landing material 45 defines a first edge 94 and a second edge 95. The first edge 94 is proximate the front waist edge 41 and the second edge 95 is remote from the front waist edge 41. The fastener landing material 45 (functioning as the cover 56) has a periphery 57 and is operatively joined about the periphery 57 to the outercover 32 (functioning as the backing 59) in the front portion 22 to form an enclosure 60 which defines a pocket 61. The pocket 61 contains one or more objects 62 therein. The enclosure 60 is illustrated in a closed condition.

The enclosure 60, in this embodiment, has a single seam 64 located in the fastener landing material 45 and extending generally in the longitudinal direction 48 from the first edge 94 to the second edge 95 of the fastener landing material 45. The seam 64 is perforated or otherwise weakened to facilitate manual tearing generally along and proximate the seam 64. As illustrated in FIG. 6, the seam 64 may have an irregular shape.

The enclosure 60 includes an object 62, such as, for example, one or more baby wipes. A caregiver or user desiring to access the one or more objects 62 located in the enclosure 60 may manually separate the seam 64 thereby transitioning the enclosure 60 from the closed condition to the open condition. In the open condition, the one or more objects 62 may be accessed and/or removed from the enclosure 60. In the open condition, one or more objects 62 may be added to the enclosure 60.

Figure 7:
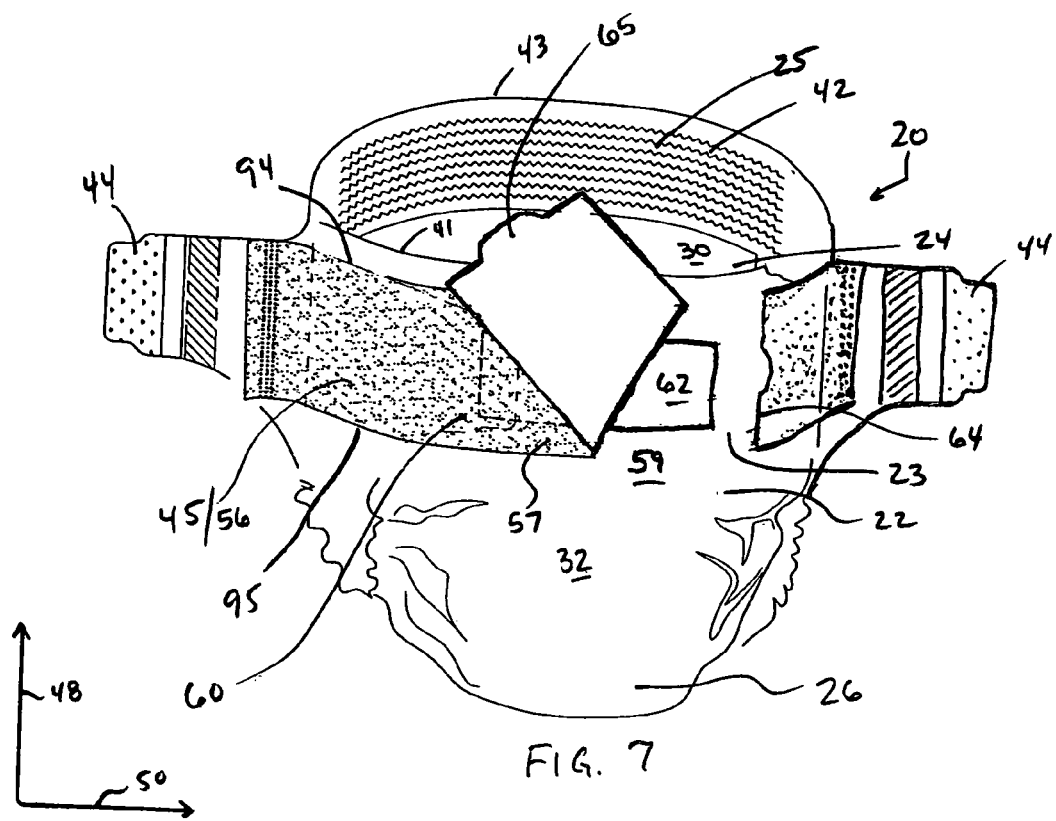
FIG. 7 representatively illustrates a front perspective view of the absorbent article of FIG. 6 with the enclosure in the open condition.

Referring now to FIG. 7, a front perspective view of the absorbent article 20 of FIG. 6 is shown with the enclosure 60 in the partially open condition thereby allowing access to the object 62 contained therein. The irregular seam 64 of this embodiment results in a tab 65 being formed after the seam 64 is broken. Also, since the seam 64 completely traverses the fastener landing material 45 in the longitudinal direction, the fastener landing material 45 separates into two pieces when the enclosure 60 is in the open condition.

Figure 8:
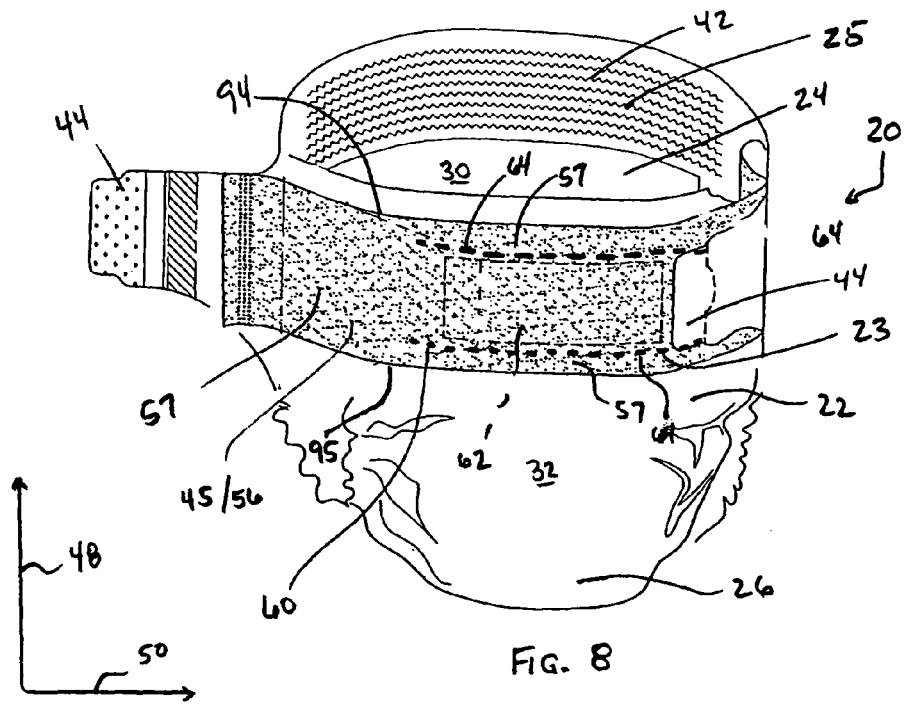
FIG. 8 representatively illustrates a front perspective view of an exemplary absorbent article having an enclosure in the closed condition.

Referring now to FIG. 8, a front perspective view of an exemplary absorbent article 20 is shown in a partially fastened condition. Similar to the absorbent article 20 of FIG. 6, the absorbent article 20 of FIG. 8 includes a front portion 22, a rear portion 24, a crotch portion 26, a front waist region 23, a rear waist region 25, and a rear waist elastic 42. The absorbent article 20 further includes a bodyside liner 30, an outercover 32 and an absorbent core 34 located between the bodyside liner 30 and the outercover 32. The absorbent article 20 further includes fastening means 44 located in the rear portion 24 that are adapted to join with a fastener landing material 45 located in the front portion 22.

The fastener landing material 45 defines a first edge 94 and a second edge 95. The first edge 94 is proximate the front waist edge 41 and the second edge 95 is remote from the front waist edge 41. The fastener landing material 45 (functioning as the cover 56) has a periphery 57 and is operatively joined about the periphery 57 to the outercover 32 (functioning as the backing 59) in the front portion 22 to form an enclosure 60 which defines a pocket 61. The pocket 61 contains one or more objects 62 therein. The enclosure 60 is illustrated in a closed condition.

The enclosure 60, in this embodiment, has a single U-shaped seam 64 located in the fastener landing material 45 and extending in both the longitudinal direction 48 and the lateral direction 50. The seam 64 is perforated or otherwise weakened to facilitate manual tearing generally along and proximate the seam 64. As illustrated in FIG. 8, the seam 64 may have an irregular shape.

The enclosure 60 includes an object 62 which may be accessed by manually separating the seam 64 and peeling the cover 56 from the backing 59 thereby transitioning the enclosure 60 from the closed condition to the open condition.

Figure 9:
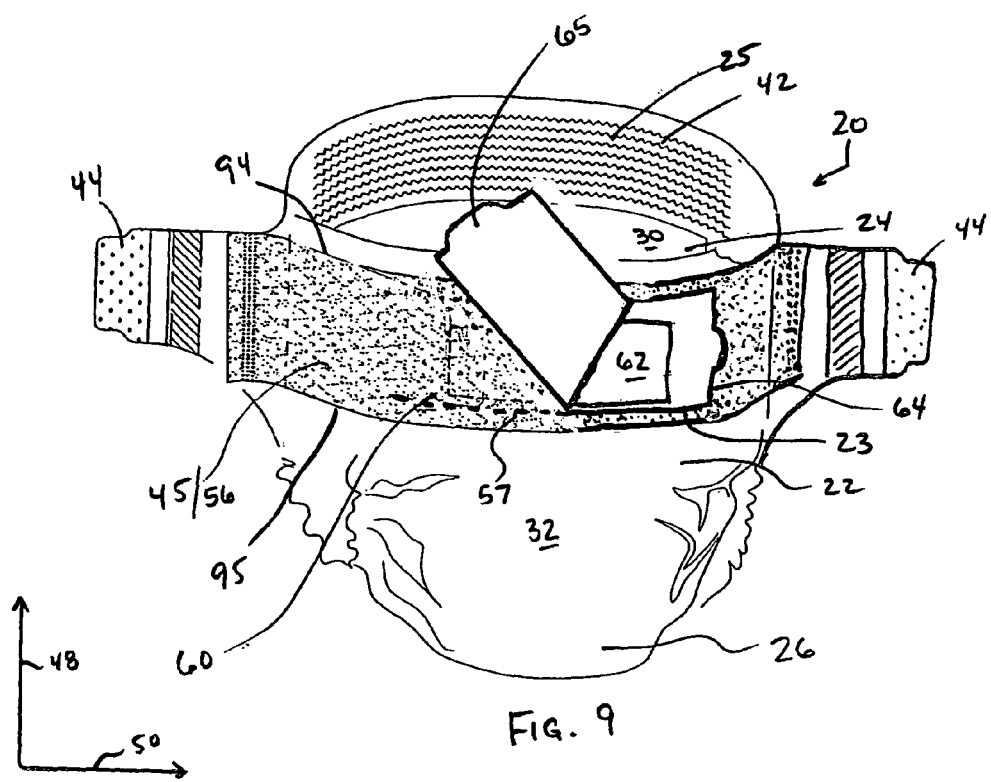
FIG. 9 representatively illustrates a front perspective view of the absorbent article of FIG. 8 with the enclosure in the open condition.

Referring now to FIG. 9, the absorbent article 20 of FIG. 8 is shown with the enclosure 60 in the partially open condition thereby allowing access to the object 62 contained therein. The irregular U-shaped seam 64 of this embodiment results in a tab 65 being formed after the seam 64 is broken. Also, since the seam 64 is U-shaped, a flap forms within the fastener landing material 45 when the enclosure is in the open condition.

Figure 10:
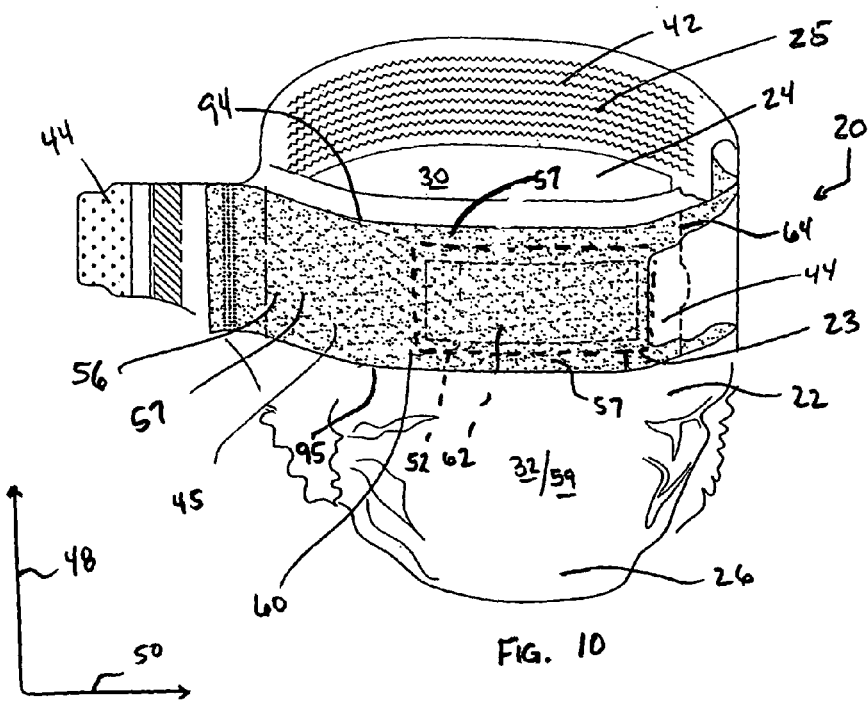
FIG. 10 representatively illustrates a front perspective view of an exemplary absorbent article having an enclosure in the closed condition.

Referring now to FIGS. 10 and 11, a front perspective view of an exemplary absorbent article 20 with an enclosure 60 is shown in the closed condition and the open condition respectively. The absorbent article 20 includes a front portion 22, a rear portion 24 and a crotch portion 26. The crotch portion 26 connects the front portion 22 to the rear portion 24. The front portion 22 includes a front waist region 23. The rear portion 24 includes a rear waist region 25. The front waist region 23 includes a front waist elastic 40. The rear waist region 25 includes a rear waist elastic 42.

The absorbent article 20, in this embodiment, further includes a bodyside liner 30, an outercover 32 and an absorbent core 34 located between the bodyside liner 30 and the outercover 32. The absorbent article 20 further includes fastening means 44 located in the rear portion 24 that are adapted to join with a fastener landing material 45 located in the front portion 22.

The enclosure 60 comprises a cover material 56 (the fastener landing material 45) having a periphery 57. The enclosure also comprises a backing material 59 (the outer cover 32) joined with the cover 56 at least about the periphery 57. The enclosure 60 defines a pocket 61 containing a package 52. The package 52 includes a sub-cover 54 having a periphery 72. The package 52 also includes a sub-backing 58. The sub-cover 54 is joined to the sub-backing 58 at least about the periphery 72 to form a second pocket 63 which contains at least one object 62 therein. The package 52 defines a closed condition and an open condition.

The sub-cover 54 and the sub-backing 58 may be joined together by any means known to those skilled in the art, such as, for example, adhesive bonds, cohesive bonds, sonic bonds, thermal bonds, mechanical bonds, and the like, and combinations thereof. The sub-cover 54 and the sub-backing 58 may be separated by application of manual force, such as, for example, peeling the sub-cover 54 away from the sub-backing 58. In some embodiments, the sub-cover 54 and the sub-backing 58 may be resealable.

The sub-cover 54 may or may not be joined with the cover 56 in various embodiments. In embodiments wherein the sub-cover 54 is joined with the cover 56, as illustrated in FIG. 11, transitioning the enclosure 60 from the closed condition to the open condition may also transition the package 52 from the closed condition to the open condition. In embodiments wherein the sub-cover 54 is not joined with the cover 56, transitioning the enclosure 60 from the closed condition to the open condition allows access to the package 52 which would be in the closed condition.

Referring again to FIG. 11, the package 52 is joined between the fastener landing material 45 (functioning as the cover 56) and the outercover 32 (functioning as the backing 59) in the front portion 22. The fastener landing material 45 has a seam 64 that is manually separable to allow a portion of the fastener landing material 45 to be lifted away from the outercover 32. The sub-backing 58 of the package 52 is joined with the outercover 32 to maintain the package 52 within the pocket 61. The sub-cover 54 of the package 52 is joined with the fastener landing material 45 such that when the fastener landing material 45 is lifted away, the sub-cover 54 is also lifted away thereby transitioning both the enclosure 60 and the package 52 from the closed condition to the open condition. In the open condition, the object 62 may be accessed.

Alternatively, the sub-cover material 54 may be unattached to the fastener landing material 45 such that when the fastener landing material is lifted away, the sub-cover material 54 remains joined with the sub-backing 58. Once the fastener landing material 45 is lifted away, the sub-cover material 54 may be manually separated from the sub-backing 58 thereby allowing access to the object(s) 62 disposed therebetween.

Figure 12:
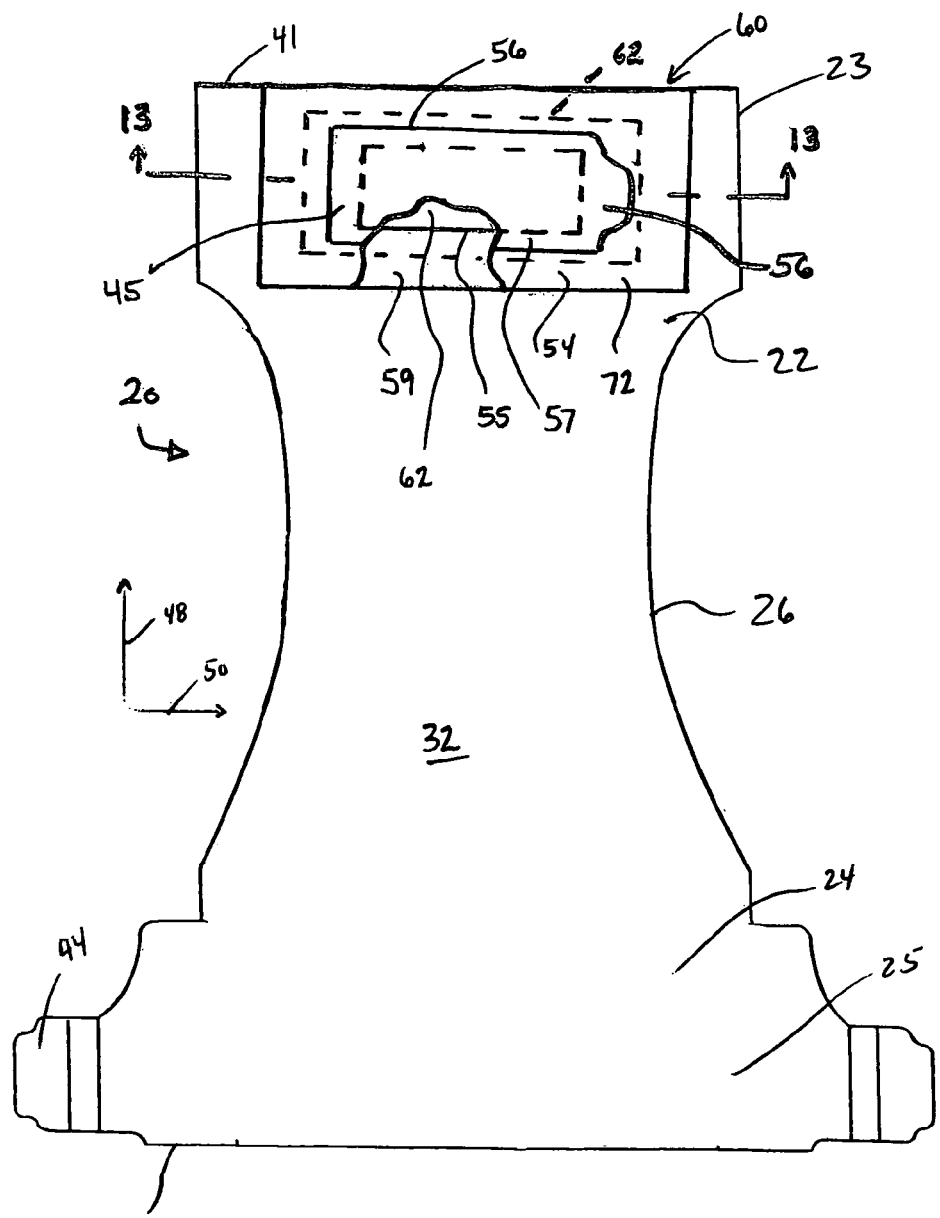
FIG. 12 representatively illustrates a partially cut away, top plan view of an exemplary absorbent article in a stretched and laid flat condition with the surface of the article that contacts the clothing of the wearer facing the viewer.
Figure 13:
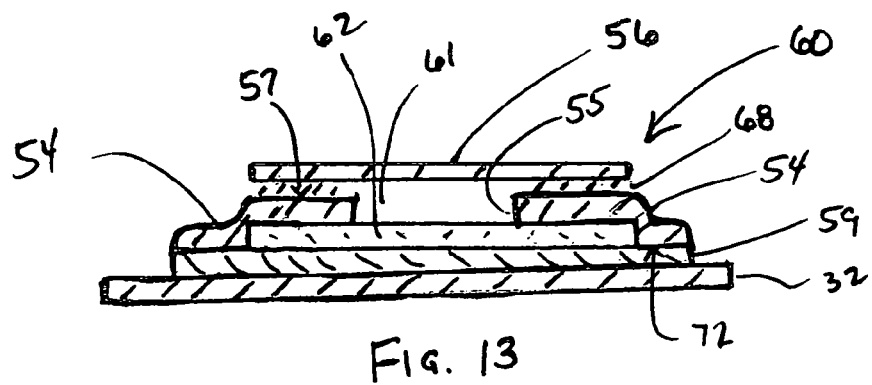
FIG. 13 representatively illustrates a cross-sectional view of the absorbent article of FIG. 12 taken along the line 13-13.

Referring now to FIG. 12, an absorbent article 20 similar to that of FIG. 1 is representatively illustrated. The article is illustrated in a laid flat condition with the surface of the article which contacts the wearer's clothing facing the viewer and with portions cut away to illustrate underlying structure. FIG. 13 is a cross-sectional illustration of the absorbent article 20 of FIG. 12 taken along the line 13-13.

Referring to FIGS. 12 and 13, the absorbent article 20 includes an enclosure 60 joined to the outercover 32 in the front waist region 23. The enclosure 60 includes a backing 59, a sub-cover 54 and a cover 56. The enclosure defines a pocket 61 which includes at least one object 62 contained therein.

The sub-cover 54 has a periphery 72 and is joined about the periphery 72 to the backing 59 to enclose an object 62 therebetween. The sub-cover 54 defines an opening 55. The cover 56 has a periphery 57 and is joined about the periphery 57 to the sub-cover 54 so as to span the opening 55 and form a lap seam 64 about the opening 55.

The cover 56 may be joined to the sub-cover 54 by any method known in the art. The sub-cover 54 may be joined to the backing 59 by any method known in the art. Preferably, the cover 56 is joined to the sub-cover 54 with a cohesive 68, such as, for example, H9078 available from Bostik having offices in Middleton, Mass., USA and Wauwatosa, Wis., USA. The cohesive 68 allows the cover 56 to be separated from the sub-cover 54 to expose the opening 55 in the sub-cover 56 and transition the enclosure 60 from the closed condition to the open condition. In the open condition, the object(s) 61 may be accessed in the pocket 61 through the opening 55. The cohesive 88 may also be adapted to transition the enclosure 60 from the open condition to the closed condition.

Preferably, the sub-cover 54 is joined to the backing 59 such that application of sufficient force to the cover 56 to separate the cover 56 from the sub-cover 54 leaves the union between the sub-cover 54 and the backing 59 intact.

While the invention has been described in detail with respect to specific embodiments thereof, it will be appreciated that those skilled in the art, upon attaining an understanding of the foregoing will readily appreciate alterations to, variations of and equivalents to these embodiments. Accordingly, the scope of the present invention should be assessed as that of the appended claims and any equivalents thereto.

The invention claimed is:

1. An absorbent article having a front portion and a rear portion, the absorbent article comprising:
- a. an outercover;
- b. a bodyside liner;
- c. an absorbent core positioned between the outercover and the bodyside liner;
- d. a fastening system comprising a pair of hook fasteners operatively joined to the absorbent article in the rear portion and a loop fastener landing material operatively joined to the outercover in the front portion, the loop fastener landing material being adapted to engage the hook fasteners to hold the article on a wearer, the loop fastener landing material being joined about a periphery to the outercover to form an enclosure,
- e. the enclosure defining a pocket and having at least one pull open seam, a closed condition and an open condition, the pull open seam being manually separable and adapted to transition the enclosure from the closed condition to the open condition upon separation; and
- f. at least one wipe disposed within the pocket, the wipe being inaccessible when the enclosure is in the closed condition, the wipe being accessible when the enclosure is in the open condition.

2. The absorbent article of claim 1 wherein the absorbent article has a longitudinal direction and a lateral direction, the seam being generally oriented in the lateral direction.

3. The absorbent article of claim 1 wherein the fastener landing material is adapted to engage the fasteners after the seam has been separated.

4. The absorbent article of claim 1 wherein the wipe disposed within the pocket is self contained within a package.

5. The absorbent article of claim 1 wherein the enclosure comprises elastic materials.

6. An absorbent article having a front portion and a rear portion, the absorbent article comprising:
- a. an outercover;
- b. a bodyside liner;
- c. an absorbent core positioned between the outercover and the bodyside liner;
- d. a fastening system comprising a pair of hook fasteners operatively joined to the absorbent article in the rear portion and a loop fastener landing material operatively joined to the outercover in the front portion, the loop fastener landing material being adapted to engage the hook fasteners to hold the article on a wearer, the loop fastener landing material being joined about a periphery to the outercover to form an enclosure,
- e. the enclosure defining a pocket and having a closed condition, an open condition, and at least one pull open lap seam joined with cohesive material, the pull open seam being manually separable and adapted to transition the enclosure from the closed condition to the open condition upon separation and wherein the enclosure is adapted to transition from the open condition to the closed condition; and
- f. at least one wipe disposed within the pocket, the wipe being inaccessible when the enclosure is in the closed condition, the wipe being accessible when the enclosure is in the open condition.

* * * * *